(12) United States Patent
Wallace (10) Patent No.: US 6,394,968 B1
(45) Date of Patent: May 28, 2002

(54) TRANS-SCLERAL METHOD AND APPARATUS FOR MEASURING INTRAOCULAR PRESSURE

(76) Inventor: David A. Wallace, 1046 Selby Ave., Westwood, CA (US) 90024

( * ) Notice: Subject to any disclaimer, the term of this patent is extended or adjusted under 35 U.S.C. 154(b) by 0 days.

(21) Appl. No.: 09/611,566

(22) Filed: Jul. 7, 2000

(51) Int. Cl.[7] ................................................. A61B 3/16
(52) U.S. Cl. ...................................................... 600/598
(58) Field of Search ................................. 600/395, 396, 600/397, 398, 399, 400, 401, 404, 405

(56) References Cited

U.S. PATENT DOCUMENTS 5,174,292 A * 12/1992 Kursar

* cited by examiner

*Primary Examiner*—Kevin Shaver
*Assistant Examiner*—Pamela Wingood

(74) *Attorney, Agent, or Firm*—Lyon & Lyon LLP (57) ABSTRACT

An instrument and method of the present invention facilitates accurate IOP determination, both before and after any laser eye treatment. A tonometer according to the present invention is specially designed to measure IOP by contacting the sclera instead of the cornea. To ensure accurate pressure measurement, the programmable logic of the tonometer assumes and compensates for normal sclera thickness, normal sclera radius of curvature, and normal sclera tissue modulus of elasticity. The tonometer preferably comprises a housing that is contoured such that it is easily grasped, in a manner of a writing pen. The functioning components of the instrument include an activation button, located on the anterior dorsal surface in close approximation to the index fingertip of the user, a liquid crystal display, a reset button, and a removable battery cover. The tip of the instrument is a solid state pressure transducer element that produces a change in voltage with a change in intraocular pressure. The electrical waveform produced by gently bringing the transducer in contact with the sclera is converted to a digital signal and processed by a microprocessor. An average pressure value and the reliability are then read out on a liquid crystal display.

15 Claims, 8 Drawing Sheets

TRANS-SCLERAL METHOD AND APPARATUS FOR MEASURING INTRAOCULAR PRESSURE

FIELD OF THE INVENTION

The present invention relates generally to the measurement of intraocular pressure, and more particularly, to a trans-scleral method and apparatus for measuring intraocular pressure.

BACKGROUND OF THE INVENTION

Measurement of intraocular pressure ("IOP") is recognized as an important component of routine eye care, as it is necessary to detect, diagnose, and assist in management of pressure-related disorders of the eye including ocular hypertension, glaucoma, or hypotony.

Devices to measure IOP appeared as early as 1926, when Schiotz introduced a device for IOP determination that employed a mobile plunger surrounded by a fixed annulus or collar. The plunger was connected to a needle pointer which, when applied to the anesthetized cornea, provided readings on an arbitrary numeric scale inversely proportional to the amount of indentation of the plunger tip relative to the annulus. The range of measurement could be shifted incrementally by changing a weight fixed to the plunger. As this device functioned by measuring the force of indentation, it is referred to as an "indentation" type tonometer. The geometry of the Schiotz device was constructed using assumptions about the normal corneal curvature radius, among other factors.

Schiotz, who coined the concept of "scleral rigidity", sensed that the inherent properties of the eye, i.e., the degree to which the wall tissues accommodate or resist deformation, might influence accuracy of the pressure measurement. He had no way to accurately measure or describe this phenomenon, but inferred that if the deformation characteristics varied away from an assumed 'normal' value, this might affect the accuracy of the measurement by his device. Since the days of Schiotz, many methods have been developed to clarify this concept. We can think of this concept in a biomechanical context, on a tissue or macro-molecular level, in terms of relative tissue elasticity, or in a strict engineering context as the modulus of elasticity.

In 1957, Goldmann introduced a tonometer device that measured eye pressure by flattening an area of central corneal tissue against a test object with known diameter. This device was referred to as an "applanation" type tonometer as it measured the force required to flatten, instead of the force required to indent, the cornea. Goldmann derived the mathematics of tip geometry for the tonometer by a combination of empirical and theoretical deductions. He found that a measurement artifact arose from at least two opposing forces, tissue rigidity and the capillary effect of precorneal tear film. When the diameter of the applanating sensor was exactly 3.06 mm, these two forces counterbalance and offset. When this state is obtained, the force of (inward) flattening exactly equals the force within the eye pushing outward, which defines IOP. To this day, the Goldmann tonometer is still the undisputed 'gold standard' embraced by ophthalmologists worldwide for routine IOP determination. It is now generally accepted that devices measuring force of indentation, such as the Schiotz tonometer, are less accurate than applanation devices like the Goldmann.

Several assumptions were made by Goldmann in the development of his applanation tonometer. He derived the geometry and tip design assuming a certain normal corneal thickness, normal corneal radius of curvature, and normal corneal tissue rigidity. Measurement accuracy of the Goldmann applanation tonometer is known to be affected by variations in these parameters away from the normal. For instance, if corneal thickness is increased or above normal, IOP measurement with the Goldmann will read high. Conversely, abnormally thin corneas are known to produce artifactually low readings.

In 1959, one of the first electronic devices for IOP measurement was introduced. This device, called the MacKay-Marg tonometer, employed an electronic strain gauge within a stainless steel transducer housing. When the transducer was applied to or removed from contact with the anesthetized cornea, the gauge produced a DC voltage offset from baseline. Pressure could be inferred from analysis of a paper tracing made by moving graph paper under a needle indicator, where needle deflection was proportional to DC current from the gauge.

The geometry of the MacKay-Marg transducer tip is different than the Goldmann tonometer. The tip consists of a central stainless steel post connected to the strain gauge, which can move relative to a surrounding stainless steel annulus. In the 'zero' state, the post protrudes a small amount from the plane of the annulus. In manufacture of the gauge transducer, this amount of protrusion is a specific distance, referred to as the offset. When enough force was applied to the post to push it level with the plane of the annulus, the condition of applanation is reached; a deflection on the DC voltage tracing can be recognized, from which IOP can be measured. The offset adopted in manufacture of this device derived in part from assumptions about the radius of curvature and modulus of elasticity of the 'normal' cornea.

In the MacKay-Marg device, the metal parts of the strain gauge transducer were not intended to touch the corneal tissue directly. They were separated from tissue by use of a latex membrane, which afforded two advantages. First, it insulated the delicate components of the strain gauge from possibly undesirable effects of moisture, debris, protein, and mucus that are present in trace amounts in normal tear film. Second, the eye being measured was protected from possible contamination and seeding of possible infectious organisms that may have been present in a prior exam.

The effects of capillary forces created by the precorneal tear film, which were important to the design geometry of the Goldmann device, could be discounted in the MacKay-Marg instrument. This allowed the tip geometry of the MacKay-Marg device to be substantially smaller than the Goldmann. The diameter of tissue flattened or applanated by the MacKay-Marg device was 1.2 mm. For this reason, the electronic tonometer was considered more accurate in conditions including central corneal scarring, distortion of corneal curvature, and after corneal transplant surgery, among others.

The Tono-Pen® tonometer, introduced in 1986, was the first hand-held, self-contained instrument to provide a digital readout of IOP. This instrument employed a stainless steel strain-gauge transducer similar to the MacKay-Marg, and electronic components including a single-chip microprocessor programmed with an 'expert system' to analyze the (digitally converted) DC voltage waveform. The Tono-Pen® and Goldmann devices are the most widely used instruments for IOP measurement in the world today. The tip geometry of the Tono-Pen® transducer is quite similar to that of the MacKay-Marg, and employs a similar latex membrane to protect both the transducer components and the cornea being measured.

Other devices have been proposed and developed to measure IOP. Non-contact devices have included those that employ puffs of pressurized air and measure the change in angle of a light reflex on the cornea. These have never been shown to have the same accuracy as contact devices, and have not been generally embraced by eye care professionals. Continuous-flow air-driven devices (the 'pneumatonometer') have been developed, and employ different assumptions about how their transducers infer IOP.

To date, all IOP measurement devices proposed and/or developed have been designed with the intent that they be used on the cornea of the eye. All are designed based on certain assumptions about the "normal" cornea, including assumptions about normal corneal radius of curvature, normal tissue thickness, and other normal tissue-specific values.

The advent of laser refractive surgery contributes new variables to the process of IOP determination. In these procedures, an excimer laser is employed to sculpt corneal tissue to precisely alter its optical properties. Laser care as rendered in photorefractive keratectomy ("PRK") and laser-assisted intrastromal keratomileusis ("LASIK") for treatment of myopia removes more tissue in the center, and less in the periphery of the cornea. This results in direct flattening of central corneal curvature, as well as decreasing central tissue thickness. Conversely, laser treatments for farsightedness (hyperopia) remove more tissue in the periphery than centrally, leading to a steepening or increase in corneal curvature.

If curvature, thickness, or tissue rigidity are altered away from the average, artifact and/or error can be introduced. At least two and possibly all three of these factors may be altered by laser refractive procedures. If the central cornea is flattened as in myopic PRK or LASIK, away from a "normal" starting radius, it will require less force to flatten the resulting surface against a flat test object. For this reason, Goldmann and other applanation devices give artificially lower readings after myopic LASIK. The converse holds true for hyperopic or steepening alterations.

Laser refractive surgery is now widely practiced in all areas of the developed world. To date, more than 5 million people have received care. With refinements in technique and laser capability, along with reduction in cost to the consumer for this care, it is likely that these numbers will steadily increase.

Therefore, it becomes increasingly important to develop instruments and methods that remain accurate for determination of IOP, both before and after any contemplated laser eye treatment.

SUMMARY OF THE INVENTION

The present invention is directed to an instrument and method that facilitates accurate IOP determination, both before and after any laser eye treatment. Because the eye is a hollow, fluid-filled structure, wherein the eye-wall comprises a cornea and a sclera, IOP can be accurately measured by an instrument that is specifically designed to measure IOP by contact against the sclera instead of the cornea. The instrument according to the present invention assumes and, within its programmable logic, compensates for certain normal sclera tissue-specific values, such as: thickness; radius of curvature; and modulus of elasticity.

The electronic tonometer of the present invention comprises a housing that is contoured such that it is easily grasped by the human hand. The tip of the instrument comprises a solid state pressure transducer element. The other functioning components of the instrument include an activation button, located on the anterior dorsal surface in close approximation to the index fingertip of the user, a liquid crystal display, a reset button, and a removable batter cover.

The measurement transducer is a solid state pressure sensitive element which produces a change in voltage with a change in intraocular pressure. The electrical waveform produced by gently bringing the transducer in contact with the sclera is converted to a digital signal and processed by a microprocessor. The microprocessor is highly interactive with the amplifier circuitry, insuring accurate data acquisition and control. The microprocessor uses multiple criteria such as slope and configuration of the waveform for accepting a reading as valid and then, while taking into account normal scleral tissue-specific values, calculates the average intraocular pressure along with an estimate of its reliability. An average pressure value and the reliability are then read out on a liquid crystal display.

Therefore it is an object of the present invention to provide the eye care professionals and general medical community with a tonometer that is reliable and accurate, both before and after any laser eye treatments, so as to assist in the diagnosis and management of ocular hypertension and glaucoma.

DETAILED DESCRIPTION OF THE PREFERRED EMBODIMENT

An instrument and method of the present invention facilitates accurate IOP determination, both before and after any laser eye treatment. The measuring device, or tonometer, of the present invention, which is specially designed to measure IOP by contacting the sclera instead of the cornea, assumes and, thus, compensates for, certain normal tissue-specific properties characteristic of the sclera. More particularly, certain programmable components adapted to compensate for normal scleral tissue thickness, radius of curvature, and modulus of elasticity are included within the tonometer's programmable logic.

The tonometer preferably comprises a housing that is contoured such that it is easily grasped, in a manner of a writing pen. The tip of the instrument is a solid state pressure transducer element. The other functioning components of the instrument include an activation button, located on the anterior dorsal surface in close approximation to the index fingertip of the user, a liquid crystal display, a reset button, and a removable batter cover.

The measurement transducer is a solid state pressure sensitive element that produces a change in voltage with a change in intraocular pressure. The electrical waveform produced by gently bringing the transducer in contact with the sclera is converted to a digital signal and processed by a microprocessor. The microprocessor is highly interactive with the amplifier circuitry, ensuring accurate data acquisition and control. The microprocessor uses multiple criteria such as slope and configuration of the waveform for accepting a reading as valid and then, while compensating for normal scleral tissue-specific properties, calculates the average intraocular pressure along with an estimate of its reliability. An average pressure value and the reliability are then read out on a liquid crystal display.

All elements of the tonometer are connected to a multi-layered circuit board. Mounted off the circuit board are four silver oxide batteries and the transducer. Mounted on the circuit board are the microprocessor, a microspeaker, and a discrete circuitry related to "wake-up" and transducer signal processing. Also on the circuit board are connectors to a display and an activiation button, and an external device interface connector.

The programmable compensation components related to certain normal scleral tissue-specific properties are preferably written into the software code loaded onto the microprocessor. However, one skilled in the art would understand that these programmable components could easily be built into any of the remaining portions of the system's programmable logic. For instance, the components could be built into the microprocessor, hardwired into the circuitry related to transducer signal processing, or built into the transducer itself.

Figure 1:
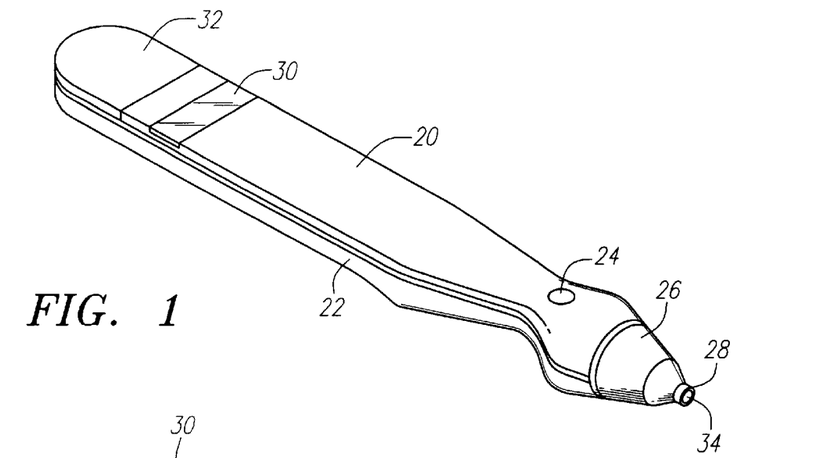
FIG. 1 is a perspective drawing of the tonometer.

FIG. 1 shows a perspective view of the tonometer 20. The tonometer 20 has a housing 22 which is formed so that a user can grasp the instrument and have his or her index finger over activation switch 24. The transducer housing 26, contains a strain gauge that is used to convert the pressure indications from the sclera to electrical impulses. The contact head 28 of the transducer housing 26 has a thin rubber membrane which covers a central post 34 (FIG. 4) attached to the strain gauge 36. After repeated measures are obtained by intermittent contact with the sclera, the pressure is then read out on the liquid crystal display 30 shown in FIG. 2.

Figure 3:
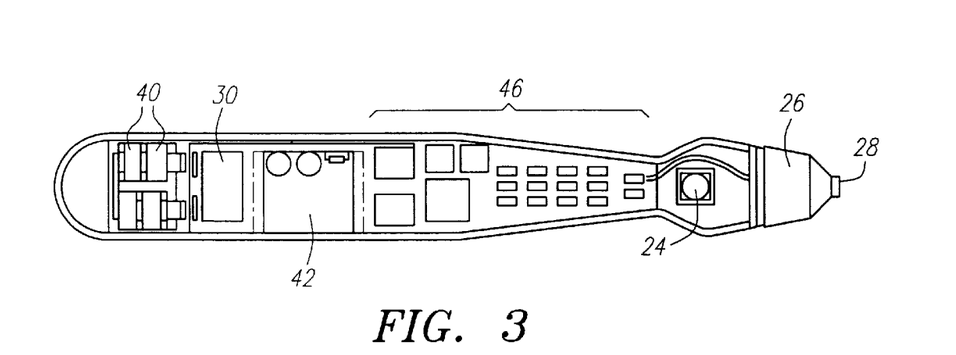
FIG. 3 is a top view of the tonometer showing the placement of the various components inside the instrument.
Figure 4:
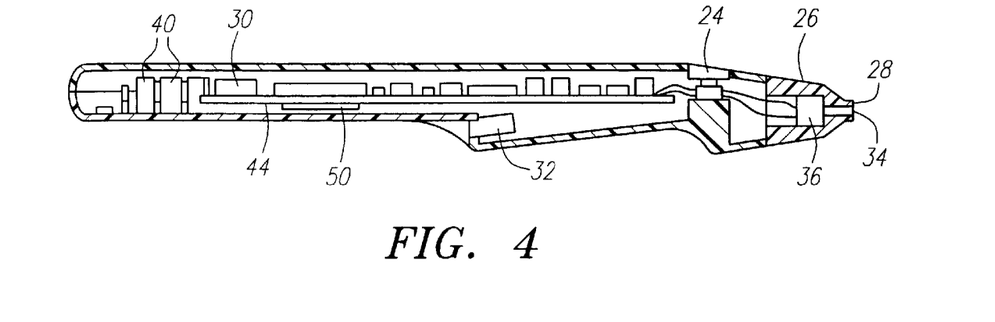
FIG. 4 is a section view of the tonometer showing component placement.

FIG. 3 is a top view of the tonometer 20 with its various components. The batteries 40 are located toward the rear of the tonometer. Adjacent to the batteries 40 is the display 30 and adjacent to the display 30 is a microprocessor 42. A three-stage high-gain amplifier 46 and its baseline reference nulling circuit are located forward of the microprocessor on a printed circuit board 44 (FIG. 4). The activation button 24 is located on the top forward portion of the instrument for easy operation by the user.

Figure 9A:
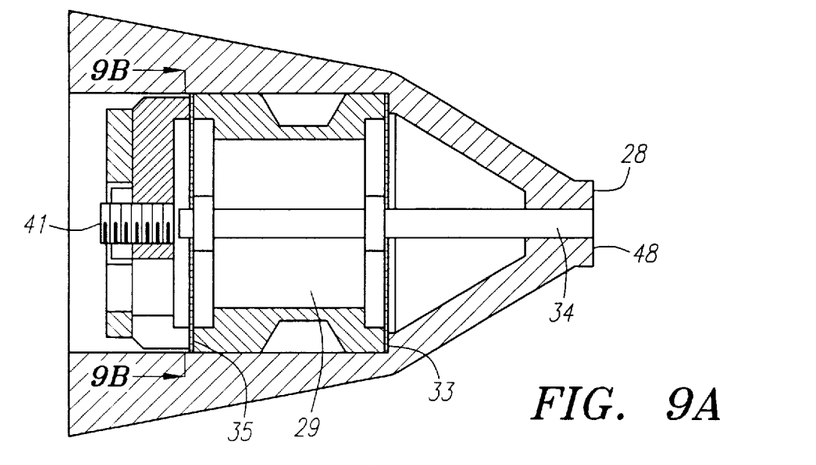
FIG. 9A is a section view of the pressure transducer and FIG. 9B is a top view of strain gauges on a plate which is shown in position in FIG. 9A by arrows 9B.
Figure 9B:
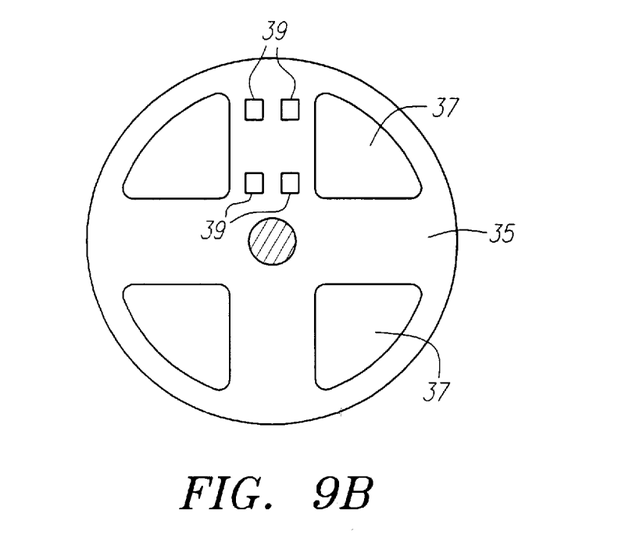

In FIG. 9A, the transducer comprises a contact head 28 and an internal assembly 29. The contact head 28 contains two components, a base 48 and a central post 34. The central post 34 is flush with the base 48, but may vary up to 0.5 microns from the base 48 without affecting the measurement. The central post 34 is welded to two flexures 33 and 35 which are 0.002 of an inch thick and one half inch in diameter. Multiple cutouts 37 are shown which serve to decrease mass while preserving strength of the elements. The anterior flexure 33 is passive, serving primarily to align the posts. The posterior flexure 35 is active in the measurement of intraocular pressure. Mounted on the flexure are four miniature impedance-matched solid state sensors 39, two of which are configured to be altered by stress and two by strain. The circuitry is configured as a wheatstone bridge. Balancing resistors and thermal correction resistors are added to the circuit, as required. A voltage of two to six volts is utilized to activate the bridge when pressure is applied to the central post 34. This force causes a change in the flexure state which is proportional to an output voltage. A stop 41 is placed posterior to the active flexure in order to protect against accidental long excursions of the post.

The central post has a mass which produces a measurable force when the transducer is moved from a "tip down" to a "tip up" position. The calibration mode is initiated by two presses of the activation button 24 in rapid succession. There is an automatic calibration of the electrical output of the transducer to an interval value representing the force supplied by gravity on the mass of the central post 34. If the discrepancy between stored and calibrated values differ by 10%, the instrument cannot be put into the measurement mode. Recalibration, however, can be attempted.

Figure 6:
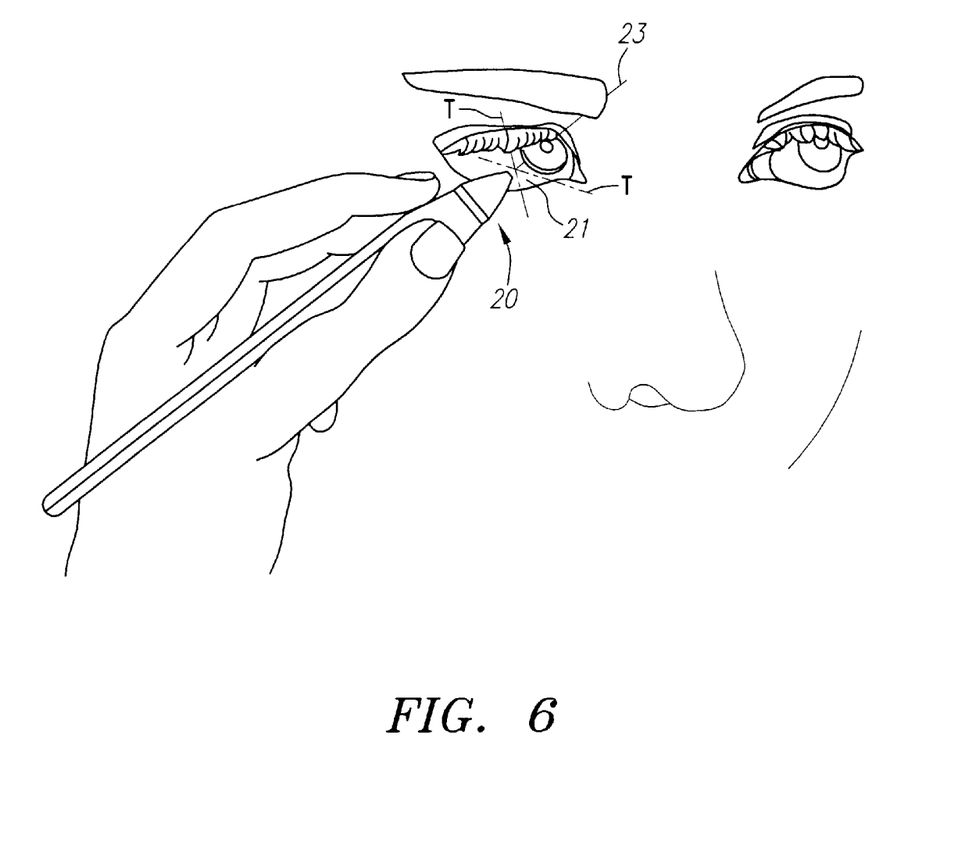
FIG. 6 is a perspective drawing of the instrument as used to make a pressure reading on a patient's eye.

The front surface of the transducer must be aligned tangent to the scleral surface at the point of contact. Referring to FIG. 6, the tonometer 20 is shown aligned with an axis 23 that is normal to the scleral surface of the eye 21. The tonometer 20 also preferably contacts the eye in the inferotemporal (lower outer) quadrant. When measuring the right eye, the transducer is brought into contact with the eye along the "7:30" meridian (i.e., the location of the hour hand on the face of a clock when the time reads 7:30). When measuring the left eye, the transducer is brought into contact with the eye along the "4:30" meridian (i.e., the location of the hour hand on the face of a clock when the time reads 4:30). Because of the variations in ocular tissue, the tonometer 20 preferably contacts the sclera of the eye at a distance in the range of about two (2) to six (6) millimeters posterior to the junction of the cornea and sclera at the desired measurement meridian. By placing the tonometer 20 in this location on the eye, the tonometer 20 will contact the scleral tissue between the inferior and lateral rectus muscles, and ensures that these and/or other extra-ocular muscles of the eye are not interposed between the transducer and the sclera, reducing the chance of artifact introduction into the process of trans-scleral intra-ocular pressure measurement.

Incomplete or off-axis contact results in slow and/or inadequate excursion of the post. When a correct applanation of the tonometer onto the eye is made, a sharply rising edge of the electrical waveform is elicited from the transducer shown as edge 90 in FIG. 8. Continuing pressure beyond that necessary to contact the sclera results in an artificial elevation of intraocular pressure by the instrument itself, shown in FIG. 8 as peak 93. At the point of optimal contact, there is a minimal indentation of the sclera by the base of the transducer tip. This results in a small transient depression 92 of voltage which best correlates with intraocular pressure as determined by manometric techniques.

Figure 8:
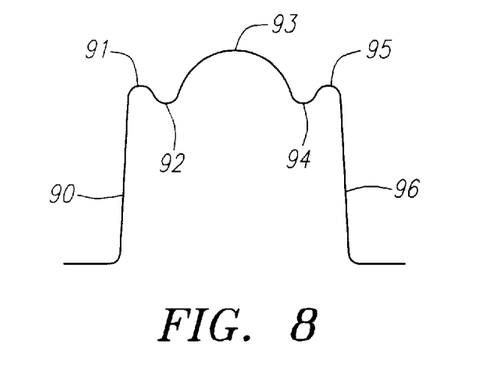
FIG. 8 is a waveform resulting from a pressure measurement.

As the transducer is removed from the sclera, a mirror image of the applanation waveform is produced such that the case of minimal scleral indentation is again achieved with a second corresponding minimum 94 in an otherwise stable voltage, following which the voltage rapidly returns to baseline as shown by falling edge 96. This waveform is shown in FIG. 8. Thus, voltage depression 92 and voltage depression 94 are substantially equivalent and best correlate with intraocular pressure.

The output voltage of the transducer 36 is ac coupled. To prevent a wandering baseline between measurements, a capacitor is shorted just prior to activating the transducer. The analog electrical signal is then digitized by the microprocessor 42 at a sampling rate of 200 to 300 Hz. Up to 32 sequential values are stored in random access memory in the microprocessor 42 and analyzed.

Figure 2:
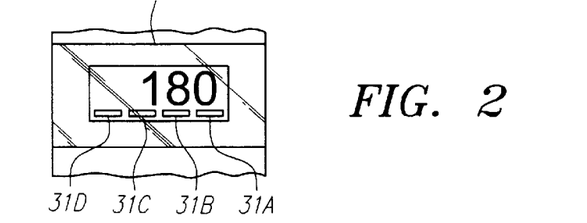
FIG. 2 is a front view of the liquid crystal display.

Analysis begins upon momentary application of the contact head 28 to the eye and consists of determining criteria for the baseline, for perpendicular application and release of the transducer to/from the sclera, and for optimal indentation. With each readable momentary application of the contact head 28 to the eye, a brief click is heard by the user, supplied by the microspeaker 50, and which is elicited by a train of electrical signals delivered from the microprocessor 42 to the microspeaker 50 mounted on the printed circuit board. All readable measures of intraocular pressure are averaged after six measurements are obtained. The range is then computed. A "beep" is given by means of a medium frequency output from the microprocessor 42 to the microspeaker 50, signaling that a reading has been obtained. The mean intraocular pressure in millimeters of mercury (Hg) is then shown on the liquid crystal display 30. One or more of four annunciator bars 31A, 31B, 31C and 31D may be illuminated denoting a correlation variance which is plus or minus 5% of the mean, shown by annunciator 31A, plus or minus 10% of the mean, shown by annunciator 31B, plus or minus 20% of the mean, shown by annunciator 31C, and greater than plus or minus 20% of the mean, shown by annunciator 31D. If ten applications of the transducer are made without achieving six readable measurements, no numeric value is displayed and the "beep" is given. The annunciator bars are shown in FIG. 2 in relationship to the display 30. At any new touch of the activation button, the microprocessor allows new measurements of intraocular pressure to be obtained. FIG. 6 shows the tonometer 20 being used to make a pressure measurement on a patient's eye 21 along an axis normal to the scleral surface of the eye as shown by dotted line 23.

Figure 5:
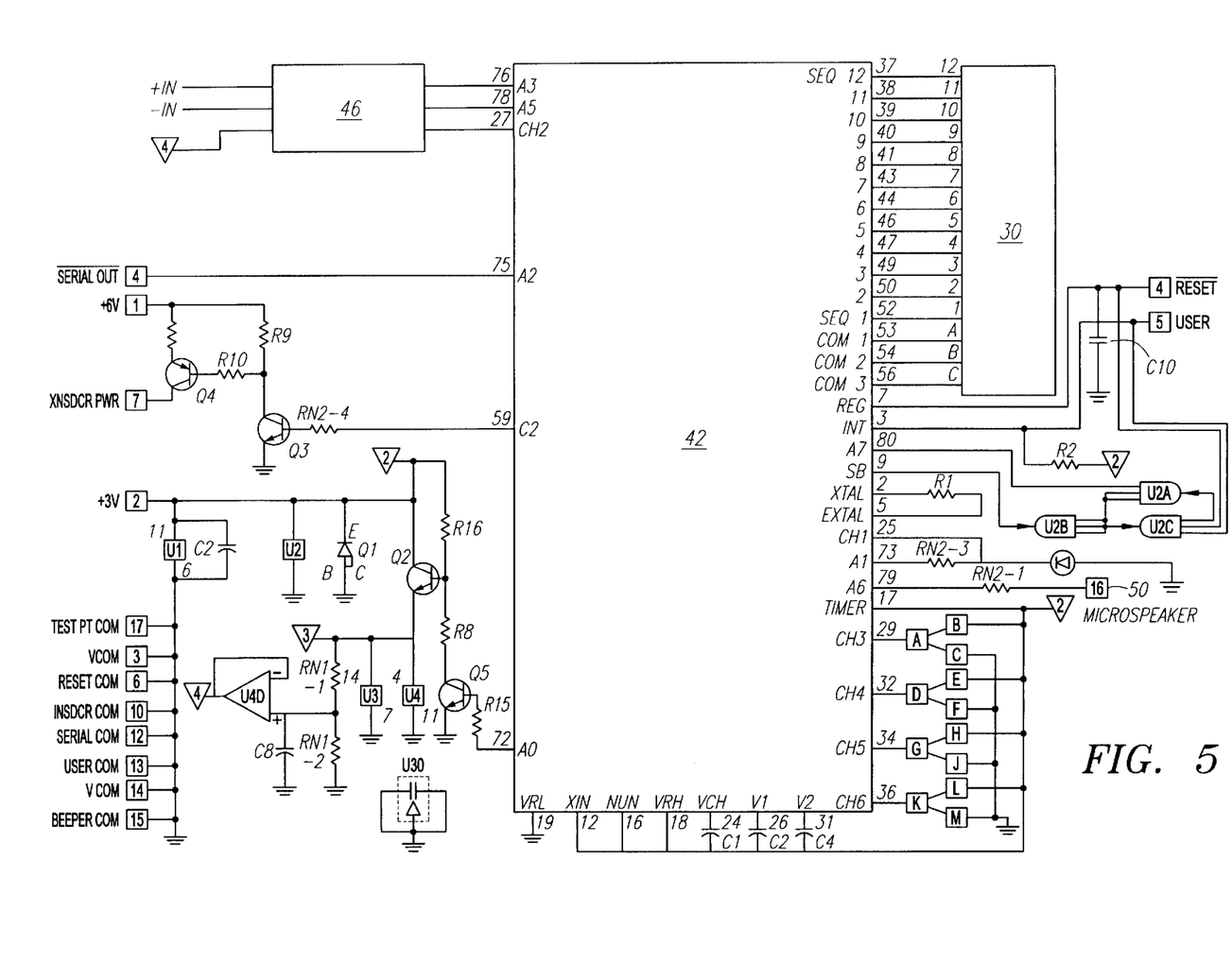
FIG. 5 is a system diagram.

FIG. 5 shows a detailed system block diagram which consists of a three-stage high-gain amplifier 46 with its associated baseline reference nulling circuit, a microprocessor 42 and a display 30. Components C1, C2, C4, C8 and C10 are capacitors; components R1, R2, RN1-1, RN1-2, RN2-1, RN2-3, RN2-4, R9, R10, R15 and R16 are resistors; components Q2, Q3, Q4 and Q5 are transistors; component U4D is an operational amplifier; components U2A, U2B and U2C are NAND gates and component 50 is a microspeaker. The strain gauge 36 (FIG. 4) is used to convert the intraocular pressure of the eye to an electrical impulse. When the contact head 28 of the transducer housing 26 is put in contact with the surface of the eye, the central post 34 of the strain gauge 36 is caused to move, which in turn causes the plate 35, on which the solid state sensors 39, are mounted to bend slightly. That in turn causes the resistance of the strain gauges 36 to increase/decrease. The strain gauge forms two of the resistive elements of a Wheatstone bridge. The output of the Wheatstone bridge is connected to the three-stage high-gain amplifier 46 where the signal is amplified for input to the microprocessor 42. The microprocessor then follows the sequence shown in the flow chart of FIGS. 10A through 10C to perform the analysis on the waveform from the three-stage high-gain amplifier 46. In that analysis, shown in the flow chart of FIGS. 10A through 10C, the dc component offset or baseline must be subtracted from the pressure waveform, shown in FIG. 8, to determine the relative differential signal of interest.

Figure 10A:
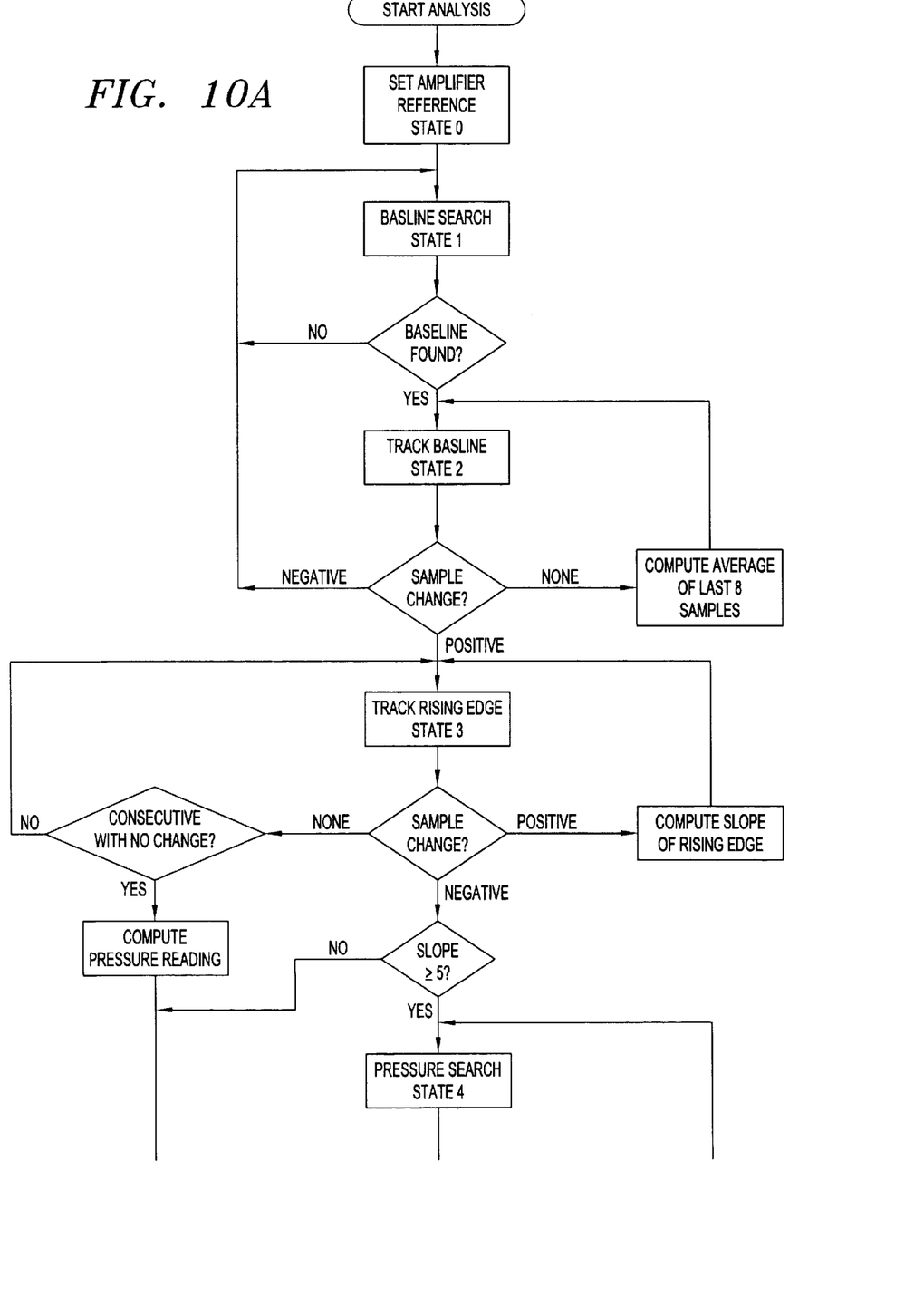
FIGS. 10A through 10C are flow diagrams of a program.
Figure 10B:
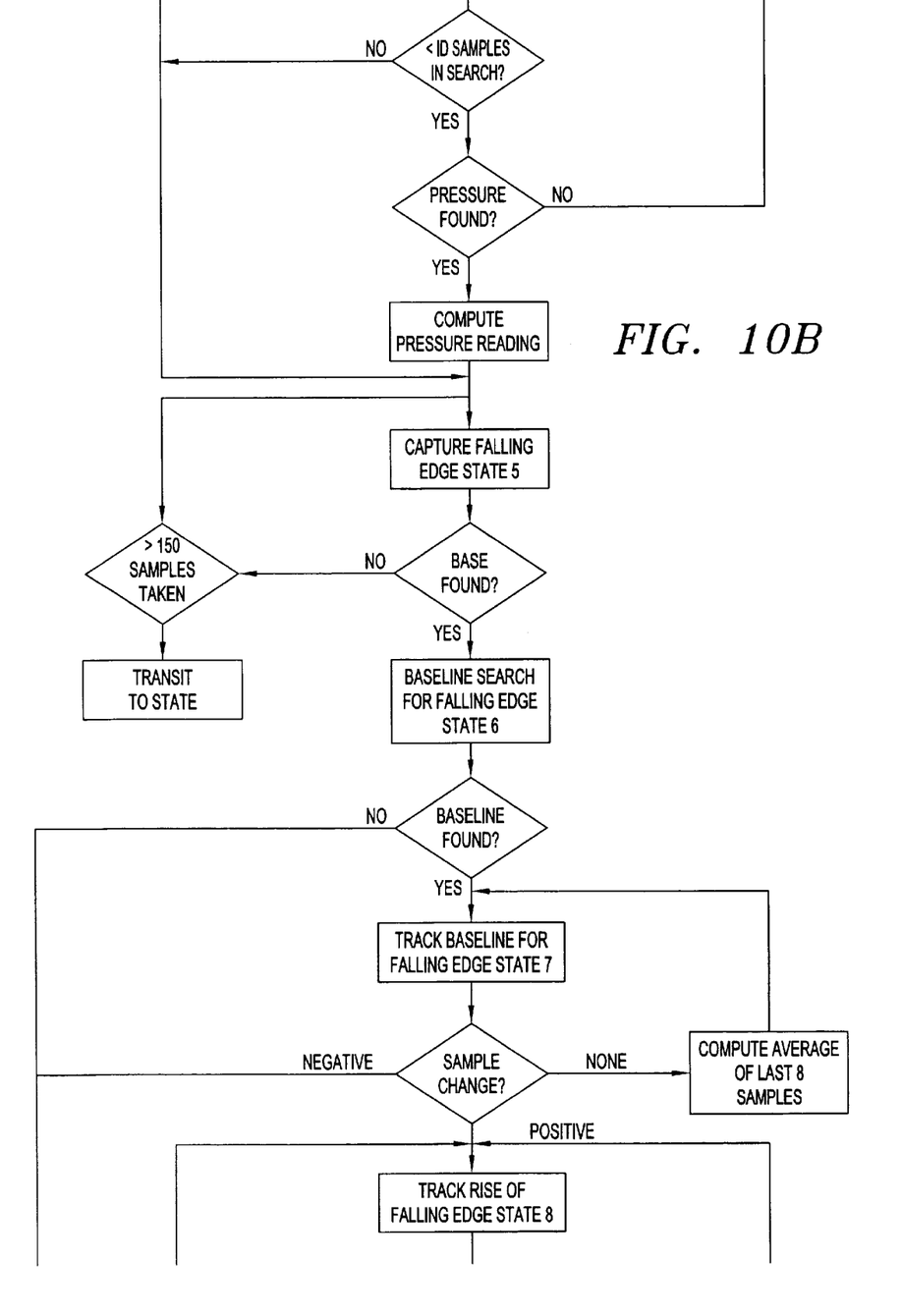
Figure 10C:
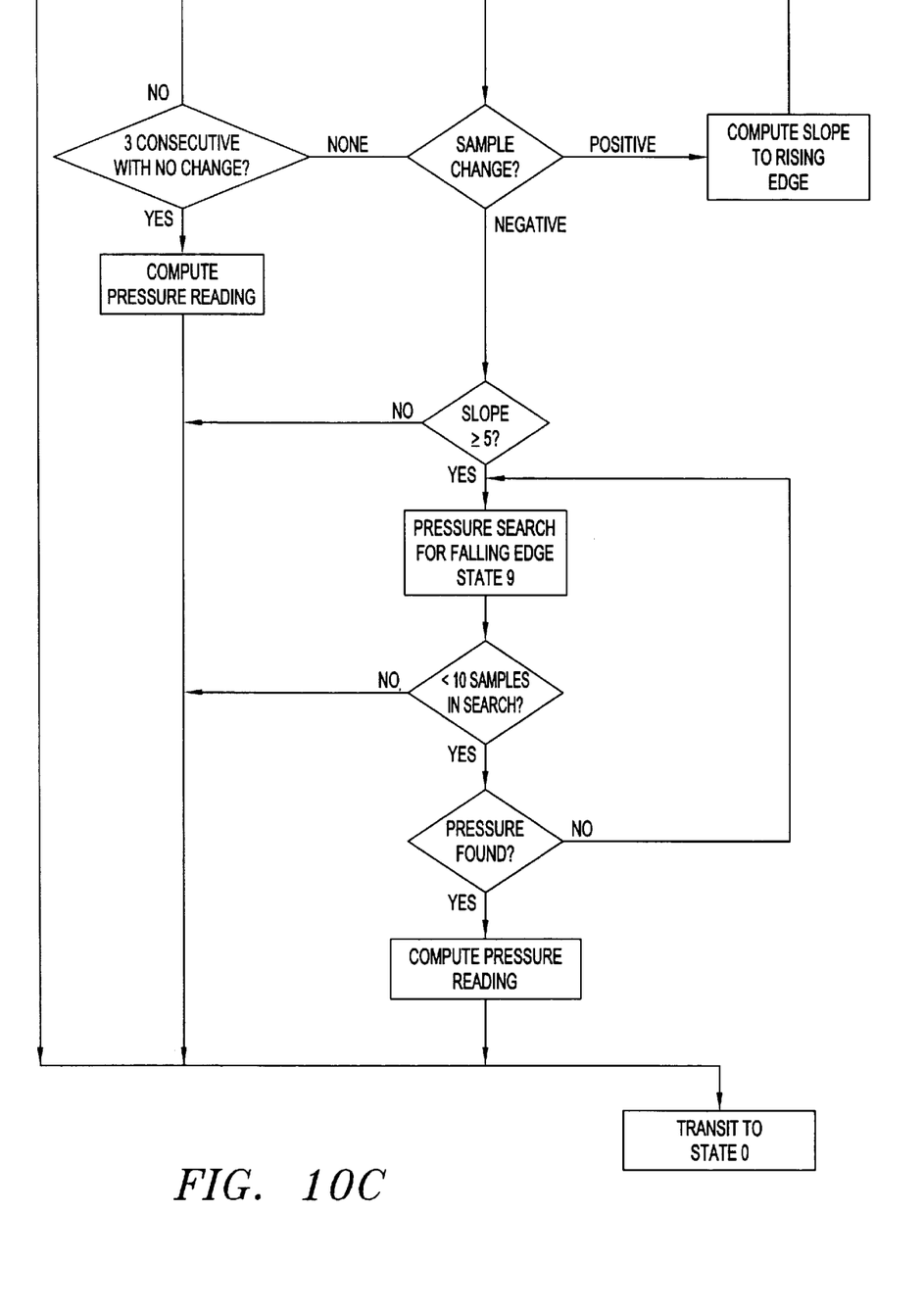

As shown in FIGS. 10A, 10B and 10C the analysis is as follows. A baseline search is initiated and then the baseline is tracked. If the change is positive, then the system tracks the rising edge. The slope of the rising edge is tracked until there is either no change or the change is negative. If there are consecutive samples in which there is no change, then a pressure reading is computed and the system then looks for a falling edge. If the slope is negative and the slope is greater than or equal to 5, then the system searches for the pressure and computes it. After the pressure reading is computed, the system analyzes for a falling edge as shown in FIG. 10B. The system then searches for a baseline. If no baseline is found, then the system exits the routine. If a baseline is found, then the baseline is tracked for a falling edge. If the sample change is negative, then the routine is exited. If there is no change, then the average of the last eight samples is computed and the system returns to the block in which the baseline is tracked for a falling edge. If the sample change is positive, then the system tracks the rising edge until there is no change or the change is, negative. If there are three consecutive "no change" readings, then the pressure reading is computed and the routine is exited. If the sample change is negative and the slope is less than or equal to 5, then the routine is exited. If the slope is greater than or equal to 5, then there is a pressure search for a falling edge. If there are greater than ten samples in this search, then the routine is exited. If there are less than ten samples, then the pressure search for the falling edge is repeated until the pressure is found at which time the pressure is computed. After the pressure reading is computed, the routine is exited.

Figure 7:
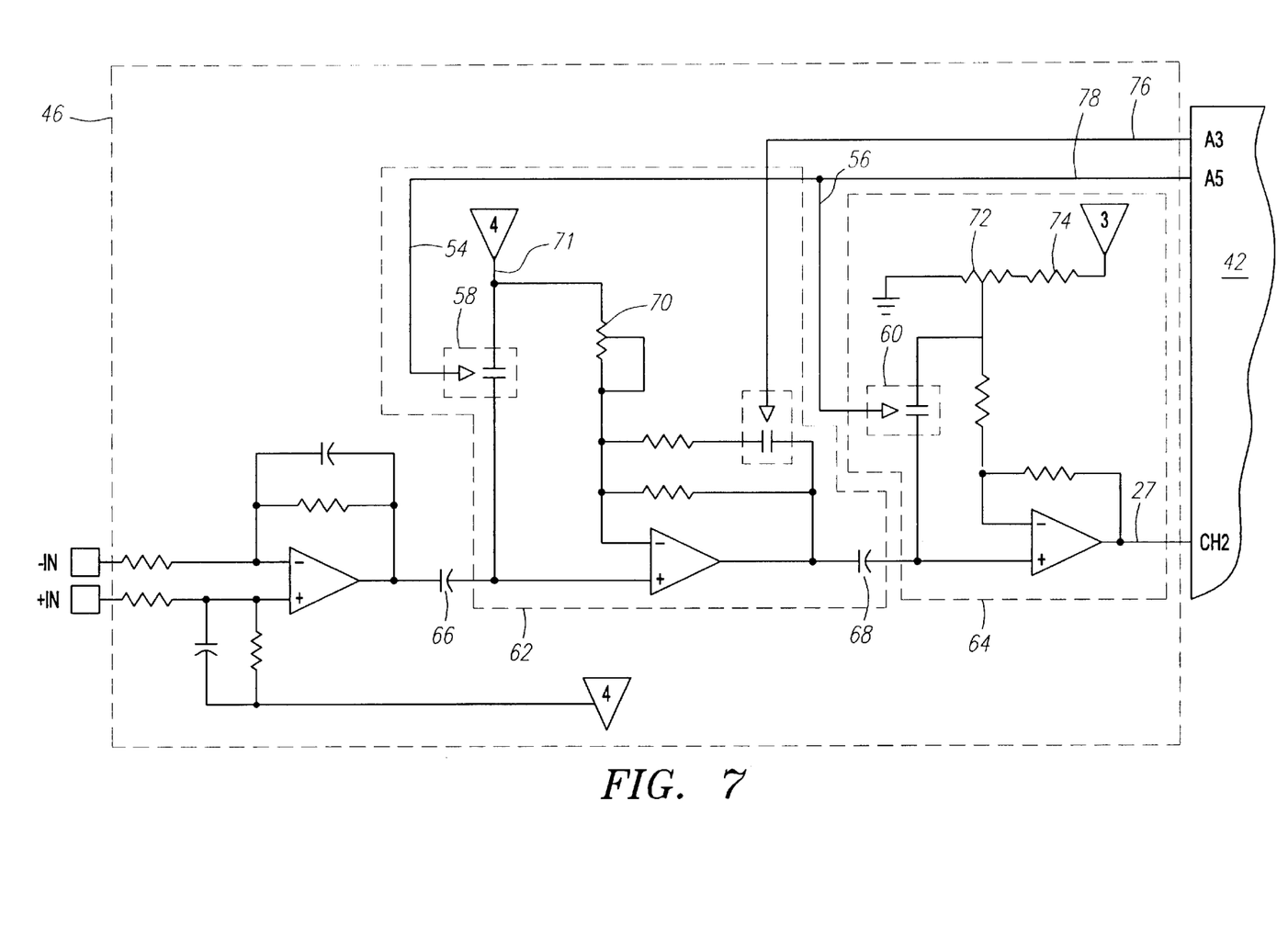
FIG. 7 is a circuit diagram of the three-stage amplifier with its associated baseline reference nulling circuit.

Referring to FIG. 7, which is a circuit of the three-stage hihg-gain amplifier 46 with its associated baseline reference nulling circuit, state 1 of the microprocessor logic involves finding a stable amplifier baseline to reference and calculate the relative amplitude of the pressure waveform shown in FIG. 8. To accomplish this, the microprocessor applies an active high (capacitor discharge) signal from lead 78 to control lines 54 and 56 of the analog switches 58 and 60 for a period of 60 mS. This nulls both the second stage 62 and the third stage 64 of the amplifier circuitry by equalizing the charge on both sides of capacitors 66 and 68. The charge of the capacitors are neutralized because there is a 1.5 volt reference voltage supplied on lead 71 which equals the reference voltage of the second stage amplifier and is applied on the second-stage amplifier side of capacitor 66. Similarly, a 0.4 volt, set by resistors 72 and 74, is directly applied to the thrid-stage side of the capacitor 68 which equals this stage's reference voltage. This neutralizing effect equalizes both differential inputs for each amplifier stage resulting in a gain of zero, and removing any carrier signal. After 60 milliseconds, the capacitor discharge signal on leads 54 and 56 is terminated, which opens both of the analog switches 58 and 60 controlled by the microprocessor 42. During the 60 millisecond time period the microprocessor is processing data already received. Mircoprocessor 42, shown in FIG. 7, is also shown as microprocessor 42 is FIG. 5.

The microprocessor is able to use the capacitor discharge control to reach the baseline when needed, while dynamically processing the pressure waveform data. The amplifiers 62 and 64 are effectively dc coupled (since there is virtually an infinite time constant) which gives the microprocessor 42 a dc level signal to process.

When the activation switch has not been depressed for twenty seconds, the microprocessor 42 and transducer elements are turned off in order to conserve power and preserve the battery life. A small discrete circuit performs this function and also responds to depression of the activation button by activating the electronic elements and the transducer.

While the preferred embodiment of the system of the present invention has been illustrated and described, certain modifications and alternatives will be apparent to those skilled in the art and the present disclosure is intended to include such modifications and alternatives within the scope of the appended claims.

What is claimed:

1. A trans-scleral method of measuring intraocular pressure comprising the steps of
   providing a tonometer having a distal tip, said distal tip includes a transducer,
   contacting the distal tip of the tonometer to the surface of the sclera of the eye being measured,
   aligning the tonometer along an axis such that the transducer can be tangent to the scleral surface of the eye being measured,
   creating an electrical waveform produced by contacting the transducer in the distal tip of the tonometer to the surface of the sclera of the eye being measured,
   converting the electrical waveform to a digital signal,
   processing the digital signal to calculate intraocular pressure,
   compensating for normal sclera tissue-specific properties, and
   calculating the intraocular pressure of the eye being measured.

2. The trans-scleral method of claim 1 wherein the normal sclera tissue-specific properties include normal sclera tissue thickness, normal sclera tissue radius of curvature, and normal sclera tissue modulus of elasticity.

3. A trans-scleral method of measuring intraocular pressure comprising the steps of:
   providing a tonometer having a distal tip,
   contacting the distal tip of the tonometer to the surface of the sclera of the eye being measured, wherein the tonometer contacts the surface of the sclera of the eye being measured in the infero-temporal quadrant and wherein the tonometer contacts the surface of the sclera of the right eye of a patient along the 7:30 meridian, and
   calculating the intraocular pressure of the eye being measured.

4. A trans-scleral method of measuring intraocular pressure comprising the steps of
   providing a tonometer having a distal tip,
   contacting the distal tip of the tonometer to the surface of the sclera of the eye being measured, wherein the tonometer contacts the surface of the sclera of the eye being measured in the infero-temporal quadrant and wherein the tonometer contacts the surface of the sclera of the left eye of a patient along the 4:30 meridian, and
   calculating the intraocular pressure of the eye being measured.

5. The method of claim 3 wherein said measuring device is applanation tonometer.

6. The method of claim 3 wherein the distal end of the measuring device includes a transducer.

7. The method of claim 6 further comprising the step of aligning the measuring device along an axis such that the transducer can be tangent to the scleral surface of the eye being measured.

8. The method of claim 6 further comprising the step of creating an electrical waveform produced by contacting the transducer in the distal end of the measuring device to the surface of the sclera of the eye being measured.

9. The method of claim 8 further comprising the step of converting the electrical waveform to a digital signal.

10. The method of claim 9 further comprising the step of processing the digital signal to calculate interocular pressure.

11. A method of measuring intraocular pressure trans-sclerally, comprising the steps of:
    contacting the sclera of an eye being measured with an intraocular pressure measuring device, compensating for normal sclera tissue-specific properties, and
    calculating the intraocular pressure of the eye being measured.

12. The method of claim 11 wherein the normal sclera tissue-specific properties include normal sclera tissue thickness, normal sclera tissue radius of curvature, and normal sclera tissue modulus of elasticity.

13. The method of claim 12 wherein components compensating for the normal sclera tissue-specific properties are embedded in programmable logic of the measuring device.

14. A method of measuring intraocular pressure trans-sclerally, comprising the steps of:
    contacting the sclera of an eye being measured with an intraocular pressure measuring device, wherein the intraocular pressure measuring device contacts the surface of the sclera of the eye being measured in the infero-temporal quadrant, and wherein the intraocular pressure measuring device contacts the surface of the sclera of the right eye of a patient along the 7:30 meridian, and
    calculating the intraocular pressure of the eye being measured.

15. A method of measuring intraocular pressure trans-sclerally, comprising the steps of
    contacting the sclera of an eye being measured with an intraocular pressure measuring device, wherein the intraocular pressure measuring device contacts the surface of the sclera of the eye being measured in the infero-temporal quadrant, and wherein the intraocular pressure measuring device contacts the surface of the sclera of the left eye of a patient along the 4:30 meridian, and
    calculating the intraocular pressure of the eye being measured.

* * * * *